United States Patent
Porro

(10) Patent No.: US 7,588,765 B2
(45) Date of Patent: Sep. 15, 2009

(54) POLYSACCHARIDE AND GLYCOCONJUGATE VACCINES

(75) Inventor: Massimo Porro, Terme-Siena (IT)

(73) Assignee: Biosynth S.r.l., Siena (IT)

( * ) Notice: Subject to any disclaimer, the term of this patent is extended or adjusted under 35 U.S.C. 154(b) by 429 days.

(21) Appl. No.: 10/513,178

(22) PCT Filed: May 7, 2003

(86) PCT No.: PCT/EP03/04948

§ 371 (c)(1),
(2), (4) Date: Oct. 29, 2004

(87) PCT Pub. No.: WO03/094959

PCT Pub. Date: Nov. 20, 2003

(65) Prior Publication Data

US 2006/0165730 A1    Jul. 27, 2006

(30) Foreign Application Priority Data

May 9, 2002    (IT) .............................. IT02/00307

(51) Int. Cl.
*A61K 39/02* (2006.01)
*G01N 33/53* (2006.01)
(52) U.S. Cl. ...................... 424/190.1; 435/7.1; 435/7.2
(58) Field of Classification Search .............. 424/190.1
See application file for complete search history.

(56) References Cited

U.S. PATENT DOCUMENTS 5,306,492 A    4/1994    Porro
6,951,652 B2 *  10/2005  Porro ...................... 424/234.1

FOREIGN PATENT DOCUMENTS

EP    0 306 607    3/1989
WO    WO 93/13797   7/1993

OTHER PUBLICATIONS

Velucchi et al (Journal of Endotoxin Research 4(4): 261-272, 1997).*
Ellis, R.W. (Chapter 29 of "VACCINES" [Plotkin, S.A. et al. (eds) published by W.B. Saunders company (Philadelphia) in 1988.*
Boslego et al. (1991).*
Ramsay et al. (Vet. Pathol vol. 42, 492-495 , 2005 ).*
GU and Tsai ( Infection and Immunity, vol. 61, No. 5, pp. 1873-1880, May 1993).*

* cited by examiner

*Primary Examiner*—Robert B. Mondesi
*Assistant Examiner*—Khatol Shahnan-Shah
(74) *Attorney, Agent, or Firm*—James V. Costigan; Hedman & Costigan, P.C.

(57) ABSTRACT

The present invention concerns a conjugation process for coupling a endotoxin (LPS) free polyfunctional polysaccharide with a polyfunctional carrier protein with quantitative yields. The invention also provides for vaccine formulations comprising the glycoconjugate antigen manufactured by the process.

13 Claims, No Drawings

```
SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: synthetic peptide

<400> SEQUENCE: 1

Cys Lys Lys Leu Phe Lys Cys Lys Thr Lys Ile
1               5                   10
```

POLYSACCHARIDE AND GLYCOCONJUGATE VACCINES

BACKGROUND

Glycoconjugate vaccines date their Industrial development for human use back to 1990, on the basis of theoretical studies and molecular models originally reported between 1929 and 1940. Those studies were re-evaluated and advanced at molecular level in the decade 1980-1990, taking advantage of the newer methodologies under development in the biotechnology Era.

The strategy of using as a vaccine a semi-synthetic antigen involving a carbohydrate covalently bound to a carrier protein, have had the experimental base in the demonstration that the immune system of human infants is not completely mature until over 2 years of age, so that highly purified Polysaccharide antigens are not efficiently recognized as foreign antigens by the human host. As a result, an adequate amount of functional, anamnestic, IgG antibody do not follow to the injection of multiple Polysaccharide injections. The carrier protein does have the function to properly prime and boost the population of helper T-cells of the host's immune system which then results in the expansion of the B-memory cell secreting serum IgG antibodies specific for the carried Polysaccharide as well as for the carrier Protein. The impact of glycoconjugate vaccines on Public Health since the early Nineties, has been invaluable as they have saved millions of children's lives at risk of deadly acute infections, like spinal meningitis due to Gram-positive and Gram-negative bacteria (*Streptococcus pneumoniae, Haemophilus influenzae, Neisseria meningitidis*).

Several strategies of chemical conjugation are known for industrially preparing a protein-carbohydrate conjugate antigen. The known techniques are unsatisfactory as to the quantitative yields.

In accordance to an aspect, the present Application deals with a preparation method which provides for:
A) the use of rigorously Endotoxin-free (LPS-free) Polysaccharide antigens, to be conjugated to a carrier protein, for an improved purity of the antigens as well as for their improved safety behaviour;
B) a quantitative yield of each reaction step involved in the process, which then results in an overall yield of the glycoconjugate antigen quantitative with respect to both components of the conjugate, that is the carrier protein and the carried carbohydrate;
C) a flexible conjugation procedure. Specifically, the conjugation process allows the synthesis of glycoconjugates as mono-, bi- or poly-valent antigens able to simultaneously express mono-, bi- or poly-valent immunogenic characteristics.

In accordance to an aspect, the present invention provides for purification and or conjugation methods as hereinafter described and claimed in the appended claims. In particular, an embodiment of the present invention provides for a conjugation process which involves the following steps:
A. Activation of the endotoxin-free polysaccharide antigen to polyfunctional polysaccharide through a diamino-alkyl spacer introduced via:
  A1. O-de-hydrogen uncoupling obtained by introduction of reactive carbonyl groups with an oxidative agent to generate aldehyde groups in the presence of borate ions when the reaction is performed in aqueous solvent; such groups being then reacted with the diamino-alkyl spacer in the presence of a reducing agent,
  A2. linkage of the diamino-alkyl spacer to the already present reactive carbonyl residues in the form of carboxyl groups by water-insoluble carbodiimide, in the presence of organic solvents,
B. Activation of the immunogenic carrier protein via bis-succinimidyl ester of an aliphatic bicarboxylic acid, resulting in a poly-functional protein through monosuccinimdylesters of the Lysine residues,
  C1. Coupling of the activated poly-functional carrier protein to the activated endotoxin-free poly-functional polysaccharide, via the monosuccinimidylesters introduced on the Lysine residues of the protein and the amino groups introduced on the polysaccharide; or, alternatively,
  C2. Coupling of the poly-functional amino-activated polysaccharide to the carrier protein via a bis-succinimidyl ester of an aliphatic bicarboxylic acid which reacts sequencially, in the same reaction mixture, with the amino groups of the amino-activated polysaccharide and with the epsilon-amino groups of the Lysine residues of the protein.

Preferably the polysaccharide antigens are purified by a method which involves the removal of contaminating endotoxin by affinity-binding of the lipid A moiety of LPS with synthetic anti-endotoxin peptides (SAEP) having retro-inverted amino acid sequences, which results in polysaccharides having a content of endotoxin conveniently lower than 0.125 Endotoxin Unit/µg polysaccharide, equivalent to less than 0.00125% (w/w).

A PREFERRED METHOD FOR PREPARING GLYCOCONJUGATE VACCINES

Preliminary Step 1: Purification of the Polysaccharide antigen from contaminating LPS This step yields a Polysaccharide antigen of exceptionally high purity, avoiding the real possibility to conjugate to the carrier protein, in addition to the Polysaccharide, the contaminating LPS. In fact, the currently used preparations of Polysaccharides originating from the capsule of Gram-negative bacteria, may contain an amount of LPS equal to or less then 25 EU/µg Polysaccharide (Endotoxin Unit/mCg). This limit is required by the Official Pharmacopoeias releasing the specifications of the product. Since 1 EU/ml as detected by LAL assay (*Limulus Amoebocyte Lysate*) equals to an average of 100 pg/ml of purified LPS, in 1 pg of Polysaccharide antigen there is an amount of contaminating LPS of 2.5 ng. Given the fact that the immunizing dose for humans is in the range of 25-50 µg for the purified capsular Polysaccharide and between 10-25 µg for the conjugated capsular Polysaccharide, one may calculate that the host is receiving between 62.5 and 125 ng LPS/dose of capsular Polysaccharide in the former vaccine and between 25 to 62.5 ng LPS/dose of conjugated Polysaccharide in the latter vaccine.

These levels of LPS impurities present in the commercially available products, when referred on weight basis to infants and young children (4 to 8 kg of average body weight between 3 and 24 months of age) which are the target populations of the glycoconjugate vaccines, correspond to and exceed the Threshold of Pyrogenicity recently determined for LPS in humans (serum levels between 1 and 2 ng LPS/kg body weight following i.v. administration). The injection of one dose of 25-50 ug of Polysaccharide vaccine, which contain 62.5-125 ng of contaminating LPS, actually introduces in the human host of the infant an amount of contaminating LPS in the range of 15-30 ng/kg. In the case of a glycoconjugate, these figures are calculated in the range 6-15 ng/kg.

This observation explains the reason why sporadic, although detectable, pyrogenic effects are reported following immunization with capsular Polysaccharide vaccines (in the form of either free Polysaccharide or conjugated Polysaccharide), even though the general side-effects of the vaccines are mitigated by the s.c. and i.m. route of administration.

The complete purification of a capsular Polysaccharide to be used in the preparation of a conjugate vaccine, is disclosed in the present Application preferably by affinity-removal of the LPS contained in the Polysaccharide preparation using a solid support (filter membrane or glass spheres or gel-chromatographic medium) to which the Synthetic Anti Endotoxin Peptides disclosed in the U.S. Pat. No. 5,589,459 (granted on Dec. 31, 1996) are covalently linked.

Preferred Procedure

SAEP3-RIS, as an example, is a cyclic peptide with the retro-inverted amino-acid sequence:

SEQ ID NO: 1

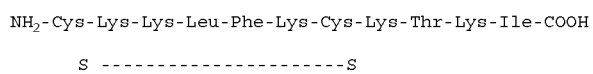

NH$_2$-Cys-Lys-Lys-Leu-Phe-Lys-Cys-Lys-Thr-Lys-Ile-COOH

S ---------------------- S which makes the peptide to be refractory to the activity of serine proteases during the purification process. SAEP3 is covalently linked to an amino-group bearing filter membrane through a known method which may include the bifunctional spacer bis-succinimidyl ester of adipic acid.

In a typical experiment, a SAEP3-RIS-activated filter membrane (pores of 0.45 μ and a density of 51.6 nmoles SAEP3/square-cm of membrane) is used as tool to remove LPS from N. meningitidis Group A Polysaccharide (PsA) solution (100 mg/ml) in PBS pH=7.20. The removed amount of LPS after a filtration cycle exceeds 2.0 logs with respect to the amount contained in the starting material (25 EU LPS/μg PsA before affinity-filtration as compared to less then 0.125 EU LPS (the sensitivity level of the LAL clot test)/μg PsA after affinity-filtration, equivalent to less than 0.00125% on weight basis. Thus, even if the affinity-filtered Polysaccharide is used at the maximum human dose administrable of 25 μg as conjugated polysaccharide (Ps) or 50 μg as pure Ps, it cannot reach the Threshold of Pyrogenicity on weight basis as the actual endotoxin level falls between 0.06 and 0.15 ng/kg, respectively, in infants and children of 4-8 Kg of average body weight. At this level of purity, the polysaccharide or glycoconjugate vaccine would not result pyrogenic even if it were injected intravenously.

An affinity-filtered PsA shows, therefore, a safer profile with respect to the Polysaccharides today recommended for vaccination as either free Ps or conjugated Ps which, although purified at high levels, still retain a non negligible amount of contaminating LPS.

Step 2: Strategic, quantitative, introduction of reactive amino groups in selected carbohydrate residues within a polysaccharide structure featuring reactive carbonyl groups in the form of either "ad hoc" introduced aldehyde groups or already present carboxyl groups Rationale Polysaccharide structures that have no potentially reactive amino groups to be used for direct conjugation strategies to a given Protein carrier, must be formerly activated by chemical reactions. It is well known from classic organic chemistry that vicinal hydroxyl groups present in a mono- or poly-saccharide structures can be activated to reactive aldehyde groups through the use of oxidizing reagents like sodium periodate in the presence of a reducing agent which stabilizes the Schiff's base formed (the classic reaction known to chemists as "reductive amination"). In previous patented procedures, this reaction has been used to directly conjugate a periodate-oxidized Ps to a given carrier Protein (Jennings 1980 and Anderson, 1982). The limit of this procedure is that the yield of reaction. is penalized by the sterical hindrance of two large molecules that must interact, that is the Ps and the Protein.

In accordance with an embodiment of the present procedure it is used the classic "reductive amination" reaction to selectively activate the Ps structure in "selected regions", by introducing a reactive amino group which preferably is spaced from the carbohydrate through an alkyl spacer (alkyl diamine) just necessary to by-pass the steric-hindrance phenomena which occur in the following conjugation step. This strategy quantitatively achieves the activation of the Ps structure. The "selected regions" of the Ps structure are conveniently represented by the vicinal, O-acetyl free, oxidryl residues forced to assume the cis-conformation by the presence of Boron ions that form complexes only with vicinal, cis-OH and not with the trans-OH. In such a way, the oxidative reaction and the consequent reduction of the Schiff's base formed, which leads to the introduction of reactive amino groups in the selected regions of the Ps structure, will preferentially take place in the cis-OH positions of the Ps structure.

An alternative strategy to the above reported, for introducing vicinal aldehyde groups in a polysaccharide featuring vicinal —OH groups, conveniently comprises the reaction of the polysaccharide antigen with the reagent lead tetra-acetate. In this case, the aqueous solvent is replaced by an organic solvent.

In accordance with another embodiment, in cases where the vicinal —OH positions are naturally present as ester-derivatives of acetyl groups (O-acetyl groups), the de-O-acetylation can be selectively and quantitatively achieved by hydrolysis with anhydrous hydrazine. Then, activation of the O-deacetylated vicinal groups follows according to the above reported procedure.

According to a further embodiment, in cases where carbonyl groups are already present in the Polysaccharide structure, in the form of carboxyl groups, the transformation to reactive amino groups is performed through the use of the above mentioned alkyl-spaced diamine, via the reaction with carbodiimide (diciclohexyl), carbodiimide or DCC or 1-ethyl-3-(dimethylaminopropyl)carbodiimiude or EDAC) in appropriate solvent.

In the activation procedures for a carbohydrate antigen, it is important not to have significant contaminating levels of endotoxin (lipopolysaccharide, LPS) in order to avoid the parallel reaction of activation of the carbohydrate chain of this molecule and then to conjugate it to the carrier protein, with the obvious result to have a conjugate polysaccharide-protein antigen which is associated with a conjugate LPS-protein featuring toxic effects upon injection in the human host.

By way of an example are illustrated preferred procedures for introducing in a Polysaccharide structure carbonyl groups in the form of aldehyde residues to be then transformed to reactive amino groups Oxidative Cleavage In a typical example of activation of a Polysaccharide structure through primary amino groups, PsA (a homo-polymer of N,O-acetyl mannosamine 1,6 phosphate purified from *N. meningitidis* group A, which have been used as such or has been previously partly de-O-acetylated with the desired stechiometric amount of anhydrous hydrazine in tetrahydro-furane for 5 to 120 minutes at 37° C., then re-covered covered by precipitation with anhydrous acetone and washed three times) is reacted with one or the other of the following reagents:

Reagent A

Sodium periodate in at least equimolar amount with the 0.5-5% of the monosaccharides featuring vicinal —OH groups, estimated in the PsA structure by NMR (Nuclear Magnetic Resonance) analysis.

In the native PsA there is an experimentally estimated amount of monosaccharide-bearing vicinal —OH groups which ranges between 10-30% of the total monosaccharide residues.

The reaction is performed conveniently in the presence of 0.25-0.50 M Borate buffer pH=8.20, 15-30 minutes at 4° C. This reaction advantageously yields the quantitative (100%) activation to aldehyde groups of the 0.5-5% of the monosaccharide residues featuring vicinal —OH groups, which are present in the PsA structure; or:

Reagent B

Lead tetra-acetate in the same conditions above reported, except that the reaction is run in organic solvent instead stead of buffer (e.g.: dimethylsulphoxide or dimethylformammide). In this case, the insoluble aldehyde-activated Ps is recovered by low-g-centrifugation and washed three times with acetone.

Reductive Amination

Following the selection of one of the two previous steps, addition of the bi-functional spacer (1,4 di-amino)-n-butane, (as an example among a variety of bis-alkyl amine such as 1,2 ethyl amine, 1,3 propyl amine, 1,4 butyl amine), is performed at a molar excess of five to ten times the amount of reducing —CHO groups introduced in the PsA structure by selective oxidation. The complex pyridine borane, necessary to efficiently reduce and therefore stabilize the Shiff's base formed, is typically added at a molar amount two to five times higher with respect to the 1,4 diamino-butane used in reaction; the mixture is conveniently kept under magnetic stirring for 18 hours (overnight) at 4° C., pH=8.20 in 0.25-0.50 M borate buffer. Finally, sodium borohydride (same molar amount of the pyridine-borane complex) is added to the reaction mixture, for 1 hour. The oxidative reaction and the reductive amination are performed as a single-step procedure.

The yield of reaction is quantitative (100%) with respect to the 0.5-5% of the monosaccharide residues featuring vicinal —OH groups, which are present in the PsA structure. At this point of the procedure, therefore, Psa features a multi-point, primary amino group-activated, structure. Given an average MW of $2.5 \times 10^5$ for PsA, on the basis of molecular sieving followed by MALDI-TOF spectrometry or any other method for mass determination, Psa would contain about 1,000 monosaccharide residues of N-acetyl-mannosamine 1,6 phosphate.

Depending by the above stoichiometry range used in the reaction, an average number of 5 to 50 monosaccharide residues result activated by the "ad hoc-spaced" primary amino group, on an average of 1,000 monosaccharide residues. The amino-activated Polysaccharide is purified from the low-molecular weight reagents by diafiltration using a membrane with NMWL of $10^4$ and 0.25 M borate buffer pH=8.20 or by gel-permeation chromatography using Sepharose G-50. This intermediate product can be freeze-dried and stored at −20° C. or lower.

The same Applicant has disclosed in the former U.S. Pat. No. 5,306,492 granted Apr. 26, 1994 the activation of *S. pneumoniae* Polysaccharides through their single end-reducing monosaccharide residue. In that case, the reaction of reductive amination was achieved at significant yield by "shifting" the equilibrium of the acetal form (closed-ring) of the end-reducing monosaccharide residue (R'—CHOH) to the open-chain form R'—CHO (semi-acetal), by using high temperature (100°C.). This reaction yielded one-end primary amino group-activated oligosaccharides useful for coupling to a carrier protein. According to this strategy, the glycoconjugate model achieved was the one corresponding to the one-end, covalently bound, oligosaccharide with no possibility of cross-linking (multiple points of covalent binding) between the oligosaccharide and the carrier protein.

Exemplary procedure for introducing reactive amino groups in a Polysaccharide structure containing carbonyl groups in the form of carboxyl residues:

Polysaccharides featuring in their structure carbonyl groups in the form of carboxyl residues (e.g.: the capsular Ps of *Salmonella typhi*, known as Vi antigen, which is a homopolymer of N,O-acetyl galatturonic acid), are activated to reactive amino groups as follows: the Vi Polysaccharide (PsVi) is solubilized in DMSO (other polysaccharides may be solubilized also in DMF or dioxane depending from their structure) and added of the bi-functional spacer 1,4diamino-n-butane (as an example) in stoichiometric amount with the 0.5-5% of the —COOH present in the Polysaccharide structure. The water-insoluble, reagent DCC (diciclohexyl carbodiimide) is added in at least equimolar amount with the bi-functional spacer. The reaction mixture is run 2-4 hours at 37 degree C. During the reaction, one mole of insoluble dicyclohexyl urea is formed per mole of amino group-activated monosaccharide residue originally bearing one —COOH residue. As the reaction is quantitative with respect to the 0.5-5% of the monosaccharide residues bearing —COOH residues, the same quantitative amount will be transformed to reactive, spaced, amino groups. After discharging the insoluble dicyclohexyl urea, the amino-activated Vi Polysaccharide is then purified from the low-molecular weight reagents by 50-75% (v/v) Et-OH precipitation or dyalized by filtration through a filter membrane with NMWL of 10.sup.4, after dilution with 0.1 M PBS ph=7.20.

Step 3: Activation of the epsilon-amino groups of the Lysine residues of the carrier protein to reactive mono-succinimidyl derivatives Rationale A proper activation of the Protein carrier for the final coupling reaction with the activated Polysaccharide, is a strategy which allows the significant increase in the yield of this reaction. The main reason for this experimental observation is that a small, highly reactive, spacer molecule can efficiently by-pass the steric-hinderance phenomena occurring when two large molecules (polysaccharide and protein) become in very close contact for reacting to form a covalent bond. In the specific case of this Application, a bis-succinimidyl ester obtained by a bi-carboxyl acid like 1, 3 carboxyl propionic, 1,4 carboxyl butanoic, 1,5 carboxyl pentanoic and 1,6 carboxyl hexanoic is used.

Preferred Procedure

The immunogenic protein Tetanus toxoid (TT), as an example, is solubilized in the mixture dimethylsulphoxide (DMSO): 0.1 M PBS (or acetate) buffer pH =7.2 (50:50 v/v) at the concentration of 10 mg/ml or more. The amount of reactive epsilon amino groups of the Lysine residues present in the protein are estimated by a conventional chemical method (e.g.: reactivity to the TNBS reagent) on an aliquot of the reaction mixture. The reaction mixture is then added of the bifunctional spacer bis-succinimidyl ester of adipic acid (acid 1,6 carboxyl hexanoic) in equivalent molar amount with respect to the amount of amino groups estimated per mole of activated PsA to be conjugated. The reaction is left 1 hours at 37.degree. C. The product of reaction is the monosuccinimidyl derivative of the Tetanus toxoid featuring the quantitative transformation of the epsilon amino groups of the Lysine residues in highly reactive monosuccinimidyl esters of adipic acid. In these conditions, no protein-protein cross-linking occurs, as the balance between the protic/polar characteristics of the solvent are crucial to privilege the derivative reaction vs. the cross-linking reaction. The activated Protein is then ready for immediate coupling to the activated PsA as the stability of this intermediate lasts no more than 30 to 60 minutes, for a quantitative recovery of it.

Step 4: Coupling of the activated Protein to the activated Polysaccharide

Rationale

Conveniently, the primary amino group-spacer-activated Polysaccharide (in the examples given above either PsA or PsVi) is reacted with the succinimidyl ester-spacer-activated Protein. In this case, the nucleophilic nature of the former activated reagent will be chemically complemented by the labile, electrophilic, ester group of the latter reagent. The product formed is a high MW poly-saccharide-protein cross-linked conjugate. The reaction can be also performed simultaneously with heterologous activated Polysaccharides for being conjugated to the same Protein carrier (e.g.: both PsA and PsVi). The conditions of reaction remain the same. In such a case a polyvalent vaccine formulation is synthesized, which uses a single carrier protein to carry-on several different capsular Polysaccharide antigens (e.g.: *Haemophilus influenzae* type b; *Neisseria meningitidis* Group A, C, Y, W135; *Streptococcus pneumoniae* type 4, 6A and 6B, 9N, 14, 18c, 19F, 23F; *S. typhi* Vi; *K. pneumoniae* etc.).

Moreover, the same strategy and the same conditions can be applied to the conjugation of carbohydrate molecules which feature in their molecular structure, primary amino groups related to the presence of an N-unsubstituted amino sugar (e.g.: glucosamine or mannosamine or galattosamine in the place of N-acetyl glucosamine or N-acetyl mannosamine or N-acetyl galattosamine etc.) as well as to the presence of ethanolamine residues. This is the case of lipopolysaccharide (LPS or endotoxin) which, in the detoxified forms as either lipid A-de-O-acylated LPS or lipid A-deprived LPS or LPS-Synthetic Anti Endotoxin Peptide complex can be used as an immunogenic entity after conjugation to a selected carrier protein.

AN EMBODIMENT OF THE PROCEDURE

An aqueous-organic solution containing the monosuccinimidylester-activated Tetanus toxoid is mixed with the aqueous-organic solution containing the amino-activated PsA. The final solution is composed by DMSO: 0.1 M PBS (or acetate) buffer pH=7.2 (50:50 v/v). The molar composition of the reagents is such that there is equimolarity between the total amount of mono-succinimidyl ester groups present on Tetanus toxoid and the total amount of amino groups present on PsA (or the total amount of amino groups present on the multiple, heterologous, polysaccharides like PsA and PsVi). The reaction takes place 2-4 hours at 4° C., with a yield which is quantitative for both (or multiple) reagents.

The HMW conjugate antigen is then recovered by 25-50% (v/v) Et-OH precipitation or by molecular sieving through a Sepharose-6B column. In the latter case, the HMW conjugate is quantitatively (100%) recovered at the Void volume of the column while the residual solvent (DMSO) present in the mixture is retained at the Vi of the column and then discarded.

Alternatively, the purification of the conjugate from the solvent (DMSO) may be performed by dialysis through filtration using a filter membrane with NMWL of 104.

Alternative procedure of coupling, which combines Step 3 and 4 for carrying out the conjugation reaction in a single Step Rationale The careful control of the balance between the polarity and the protonic features of the solvent used as medium of reaction, allows for the possibility to effectively "drive" the coupling reaction between the amino linker-activated Polysaccharide and the carrier Protein via a bi-functional linker like the bis-succinimidyl esters of a bicarboxylic acid. In particular, an ester group is stable for several hours in a polar, non-protic, solvent like DMSO while it is quickly hydrolyzed in the presence of a polar, protic, solvent like water. Since the solubility and retention of antigenicity of Polysaccharides and several Proteins in an appropriate mixture of DMSO/Water does not represent a problem, the selection of a well balanced solvent system becomes crucial for an efficient thermodynamic of the coupling reaction. In opportune conditions of stability of the bi-functional ester reagent and for several polysaccharide and protein antigens is then possible to achieve the coupling of the two molecular entities (Polysaccharide and Protein) in a single step.

An Exemplary Procedure

The amino linker-activated Polysaccharide is solubilized at 4° C. in DMSO/0.1 M acetate buffer pH=7.0 (75%:25% v/v) at the concentration of 5-10 mg/ml and added of the bi-functional spacer bis-succinimidyl ester of adipic acid (as an example) in an amount comparable to that stoichiometrically required by the total molar amount of amino groups present in its structure (e.g.: as determined by TNBS reaction). The carrier Protein, previously solubilized at 4° C. in DMS/0.1 M acetate buffer pH=7.0 (50%:50% v/v) at the concentration of 5-10 mg/ml, is then added to the reaction mixture within a time-frame of 15 to 60 minutes from the addition of the bi-functional spacer. The total amount of amino linker-activated Polysaccharide and the total amount of carrier Protein present in the reaction mixture are in a range of (W/W) ratio between 1:1 and 1:5 and even higher, depending from the MW of the two reagents and the amount of amino groups per mole of each reagents. The reaction is kept at 4° C., under mild stirring, for additional 4-6 hours. The glycoconjugate product is then quantitatively (100% for both components) recovered according to the procedure reported for the Step 4 above, in order to remove the LMW compounds present in the reaction, that is the N-hydroxysuccinimide released during the reaction of the ester groups with the amino groups, the solvent DMSO and the acetate ions.

Stability and storage of the glycoconjugate vaccines prepared according to an embodiment of the method of the invention The resulting linker interposed between the protein and the polysaccharide antigens contains two amidic bonds and one reduced imine-bond. The former bond is found in natural proteins and can be cleaved only in hard conditions like temperature above 100° C. in the presence of 3 M HCl. The latter is resistant even in the hard conditions where the former is cleaved. Accordingly, the glycoconjugate prepared according to the above method results to be a very stable product. Above all, the glycosylation procedure also yields a more stable carrier protein to proteolysis by serine proteases like trypsin and chimotrypsin. However, since the stability of a glycoconjugate is also referred to the polysaccharide structure as such, a given Ps structure may present different requirements for the long-term storage than other structures. For this reason, the storage of a similar product is anyway recommended as freeze-dried form at −20° C. or lower, in the presence of an inert support (e.g.: lactose or mannitol, 5% w/v).

Results Obtained with an Embodiment of the Conjugation Process

Physical-Chemical

The conjugate resulting from the disclosed procedure is a cross-linked, poly-disperse and high molecular weight, entity which elutes from a molecular siever like Sepharose 2B-CL with a bell-shaped mono-modal or bi-modal curve in the range of Kd=0.1-0.8. The elution profile proves that the conjugate entity is a poly-disperse system in terms of molecular weight. The purified conjugate features an average molar ratio Protein:Polysaccharide in the range 0.75-1.25 (mol/mol). However, this ratio may vary considerably (in the range 0.5-2.0 mol/mol or higher) depending from the MW of the Protein and the Polysaccharide used in the conjugation reaction. Transferred on weight basis, the value of this ratio may vary significantly according to the MW of the components in the conjugate. In the examples given above using PsA and Tetanus Toxoid according to the described stoichiometry of reaction, the mean of the (w/w) ratio Protein:Polysaccharide may be as high as 3 with an SD value which falls within the 25% of the value.

Pyrogenicity

Such a conjugate contains less than 0.125 EU/μg of product (or less than 12.5 pg LPS/ug of conjugate, corresponding to less than 0.00125% w/w) when assayed by LAL clotting.

Yield of Reaction

The overall yield of the whole process is quantitative as referred to both the components of the conjugate.

Efficiency of the Conjugation Reaction

The synthesis reaction is very flexible, in that either monovalent or polyvalent glycoconjugate vaccines can be prepared in the same conjugation step. A list of polyvalent vaccines that may be made by the present invention includes, but is not limited, the following:

a tetravalent meningococcal group A, C, W135, Y glycoconjugate vaccine prepared by coupling each separate amino-activated polysaccharide to the same carrier protein.

a polyvalent pneumococcal group 4,6,9,14,18,19,23 glycoconjugate vaccine prepared by coupling each separate amino-activated polysaccharide to the same carrier protein.

A polyvalent meningococcal and pneumococcal glycoconjugate vaccine prepared by coupling each separate amino-activated polysaccharide to the same carrier protein.

Immunogenicity in Mice

As an example to demonstrate immunogenicity of a glycoconjugate synthesized with the new industrial process, groups of 8 weeks-old Swiss Webster (SW) mice were immunized by subcutaneous or intramuscular or intraperitoneal route with three doses of the glycoconjugate vaccine TT-PsA in the dose range 1-10 ug/mouse, two weeks apart (week 0, 2, 4). Two weeks following each injection (week 0, 2, 4, 6), mice were bled and their sera assayed by ELISA in order to quantitate the level of IgG isotype antibody specifically induced against the carried polysaccharide A and the carrier protein TT.

The following Table 1 shows the antibody titers obtained:

TABLE 1

Glycoconjugate-induced IgG ELISA titers of SW mice sera* without mineral adjuvant, nd relative biological functionality

| Dose of PsA as conjugate** | Week 0 | | Week 2 | | Week 6 | |
|---|---|---|---|---|---|---|
| (route: s.c.) | TT | PsA | TT | PsA | TT | PsA |
| 1 ug/mouse | <200 | <200 | 3,000 | 1,000 | 42,500 | 5,500 |
| | (<0.1) | (<10) | (0.5) | (32) | (5.0) | (128) |
| 5 ug/mouse | <200 | <200 | 7,200 | 4,500 | 136,900 | 25,000 |
| | | | (1) | (128) | (>10) | (1,024) |
| 10 ug/mouse | <200 | <200 | 9,600 | 5,800 | 138,500 | 26,500 |
| | | | (>1) | (128) | (>10) | (2,048) |

*Titers are expressed as the mean of the reciprocal dilution (end-point) of sera pool from groups of five mice each, from three different experiments. The SD of the mean titers fell within 20% of the reported values. The biological functionality of the antibodies is indicated in parenthesis and is referred to complement-dependent bactericidal activity (PsA) as well as to the Tetanus Toxin-neutralizing activity. PsA injected as control in the range-dose 5-10 ug/mouse, did not induce any significant amount of PsA-specific IgG antibodies (End-point Titres < 200)
**The dose of conjugate contains the two components in the same amount (2.5 ug each) as their ratio on weight basis is 1.0.

As a further example of immunization, comparable groups of mice were injected with another preparation of glycoconjugate TT-PsA, using as mineral adjuvant AlPO4:

TABLE 2

Glycoconjugate-induced IgG ELISA titres of SW mice sera*, using the mineral adjuvant AlPO4.

| Dose of PsA as conjugate** | Week 0 | | Week 2 | | Week 6 | |
|---|---|---|---|---|---|---|
| (route: i.p.) | TT | PsA | TT | PsA | TT | PsA |
| 5 ug/mouse | <200 | <100 | 800 | 1000 | 51.200 | 409.600 |
| 10 ug/mouse | <200 | <100 | 3.200 | 1.600 | 51.200 | 204.800 |

*ELISA titres expressed as in Table 1. PsA injected as control at the same dose did not induce significant titers of PsA-specific IgG antibodies (End-point Titres < 200)
**The dose of conjugate contains the two components in the w/w ratio Protein:Polysaccharide = 3.0

Preferred Dose and Formulation of Polysaccharide and Glycoconjugate Vaccines

The dose of polysaccharide in the form of glycoconjugate vaccines prepared according to the disclosed conjugation process, may vary preferably from 0.5 to 10 μg or more in infants and children and up to 25-50 ug or more in adults, when the vaccine is intended for protection against one carried Ps antigen (monovalent formulation). In cases of polyvalent formulations, that is when multiple Ps antigens are carried on by the same protein carrier or are associated as mono-valent heterologous glycoconjugates; the dose can be increased accordingly to the broad-spectrum composition of the vaccine, keeping in consideration the dose-range above reported. Those experts in the art of clinical experimentation may properly find the optimal immunizing dose.

Conveniently, the dose of polysaccharide vaccines purified according to the disclosed method may vary from 5 to 50 μg in young children. The same considerations above reported for polyvalent formulations of glycoconjugates also apply to polysaccharide vaccines. As infants do not adequately respond to polysaccharide antigens, these can be used for booster immunization after the basic immunization has been performed using glycoconjugate vaccines. Also, either the monovalent or the polyvalent formulations of polysaccharide and glycoconjugate vaccines can be associated with other commercially available paediatric vaccines with or without the presence of mineral adjuvants which may contribute to the immunogenicity of the whole formulation.

B: Activation of the immunogenic carrier protein via bis-succinimidyl ester of an aliphatic bicarboxylic acid, resulting in a poly-functional protein through monosuccinimidylesters of the Lysine residues, C: Coupling of the activated poly-functional carrier protein to the activated endotoxin-free poly-functional capsular polysaccharide, via the monosuccinimidylesters of the Lysine residues of the protein and the amino groups of the polysaccharide.

2. A conjugation process wherein said endotoxin-free capsular polysaccharide antigens is prepared by the removal of a contaminating endotoxin by affinity-binding of the lipid A moiety of LPS with synthetic anti-endotoxin peptides (SAEP) featuring retro-inverted amino acid sequences.

3. A vaccine containing one or more glycoconjugate antigens prepared, by the following steps:

A: Activation of an endotoxin-free capsular polysaccharide antigen to polyfunctional capsular polysaccharide through a diamino-alkyl spacer introduced via:

A1: O-de-hydrogen uncoupling obtained by introduction of reactive carbonyl groups with an oxidative agent to generate aldehyde groups in the presence of borate ions when the reaction is performed in aqueous solvent; said groups being then reacted with the diamino-alkyl spacer in the presence of a reducing agent, or via A2: linkage of the diamino-alkyl spacer to the already present reactive carbonyl residues in the form of carboxyl groups by water-insoluble carbodiimide, in the presence of organic solvents,

The invention claimed is:

1. A conjugation process which involves the following steps:

A: Activation of an endotoxin-free polysaccharide antigen to polyfunctional capsular polysaccharide through a diamino-alkyl spacer introduced via:

A1: O-de-hydrogen uncoupling obtained by introduction of reactive carbonyl groups with an oxidative agent to generate aldehyde groups in the presence of borate ions when the reaction is performed in aqueous solvent; said groups being then reacted with the diamino-alkyl spacer in the presence of a reducing agent, or via A2: linkage of the diamino-alkyl spacer to the already present reactive carbonyl residues in the form of carboxyl groups by water-insoluble carbodiimide, in the presence of organic solvents, B: Activation of the immunogenic carrier protein via bis-succinimidyl ester of an aliphatic bicarboxylic acid, resulting in a poly-functional protein through monosuccinimidylesters of the Lysine residues C: Coupling of the activated poly-fu notional carrier protein to the activated endotoxin-free poly-functional capsular polysaccharide, via the monosuccinimidylesters of the Lysine residues of the protein and the amino groups of the polysaccharide wherein said endotoxin-free capsular polysaccharide antigen is prepared by the removal of a contaminating endotoxin by affinity-binding of the lipid A moiety of LPS with synthetic anti-endotoxin peptides featuring retro-inverted amino acid sequences and which is administered by the subcutaneous, intra muscular and intra dermal route in the dose-range 0.1-100 ug, in single or multiple injections.

4. A vaccine formulation which contains one or more glycoconjugate antigens prepared according to claim 3.

5. A vaccine comprising a conjugate of a substantially endotoxin-free capsular polysaccharide antigen with a carrier protein according to claim 3.

6. A vaccine according to claim 5 wherein the capsular polysaccharide has a content of endotoxin lower than 0.125 Endotoxin Unit/ μg polysaccharide, equivalent to less than 0.00125% (w/w).

7. A vaccine according to claim 5 comprising a glycoconjugate antigen specific for *Neisseria meningitidis* Group A.

8. A vaccine according to claim 5 comprising a glycoconjugate antigen specific for *Neisseria meningitidis* Group C.

9. A vaccine according to claim 5 comprising a glycoconjugate antigen specific for *Neisseria meningitidis* Group W135.

10. A vaccine according to claim 5 comprising a glycoconjugate antigen specific for *Neisseria meningitidis* Group Y.

11. A vaccine according to claim 5 comprising multiple glycoconjugate antigens specific for *Neisseria meningitidis* Group A, C, W135 and Y.

12. A vaccine comprising a conjugate of an endotoxin-free capsular polysaccharide antigen with a carrier protein prepared according to steps A, B end C of claim 3, where activation is achieved by A1.

13. A vaccine comprising a conjugate of an endotoxin-free capsular polysaccharide antigen with a carrier protein prepared according to steps A, B and C of claim 3, where activation is achieved by A2.

* * * * *